United States Patent [19]

Morton, Jr.

[11] 4,066,836

[45] Jan. 3, 1978

[54] 3,7-INTER-M-PHENYLENE-4,5,6-TRINOR-PGD₁ COMPOUNDS

[75] Inventor: Douglas Ross Morton, Jr., Portage, Mich.

[73] Assignee: The Upjohn Company, Kalamazoo, Mich.

[21] Appl. No.: 755,580

[22] Filed: Dec. 30, 1976

Related U.S. Application Data

[62] Division of Ser. No. 614,242, Sept. 17, 1975, Pat. No. 4,016,184.

[51] Int. Cl.² ............................................. C05C 09/76
[52] U.S. Cl. .................................. 560/53; 260/520 R; 260/520 B; 260/520 C
[58] Field of Search ........... 260/473 R, 473 G, 520 R, 260/520 B, 520 C

[56] References Cited

FOREIGN PATENT DOCUMENTS

| 30,848 | 7/1973 | Japan | 260/473 R |
| 7,301,094 | 7/1973 | Netherlands | 260/473 R |

*Primary Examiner*—Paul J. Killos
*Attorney, Agent, or Firm*—Robert A. Armitage

[57] ABSTRACT

Prostaglandin analogs with the following cyclopentane ring structure:

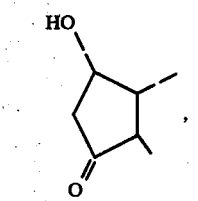

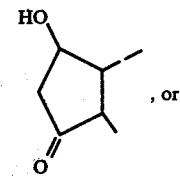

, or

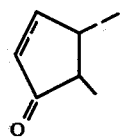

are disclosed along with intermediates useful in their preparation and processes for their preparation. These analogs are useful for the same pharmacological purposes as the prostaglandins, particularly and especially as blood platelet aggregation inhibitors.

33 Claims, No Drawings

3,7-INTER-M-PHENYLENE-4,5,6-TRINOR-PGD₁ COMPOUNDS

The present application is a divisional application of Ser. No. 614,242, filed Sept. 17, 1975, now issued as U.S. Pat. No. 4,016,184, on Apr. 5, 1977.

The present invention relates to prostaglandin analogs for which the essential material constituting a disclosure therefor is incorporated by reference here from U.S. Pat. No. 4,016,184, issued Apr. 5, 1977.

I claim:

1. A prostaglandin analog of the formula

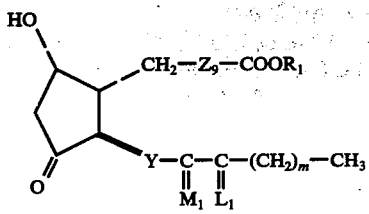

wherein Y is cis—CH=CH— or trans—CH=CH—;
wherein $m$ is one to 5, inclusive;
wherein $M_1$ is

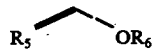

or

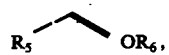

wherein $R_5$ and $R_6$ are hydrogen or methyl, with the proviso that one of $R_5$ and $R_6$ is methyl only when the other is hydrogen;
wherein $L_1$ is

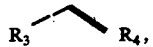

or a mixture of

and

wherein $R_3$ and $R_4$ are hydrogen, methyl, or fluoro, being the same or different, with the proviso that one of $R_3$ and $R_4$ is fluoro only when the other is hydrogen or fluoro;
wherein $R_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, phenyl substituted with one, two, or three chloro or alkyl of one to 3 carbon atoms, inclusive, or a pharmacologically acceptable cation; and
wherein $Z_9$ is

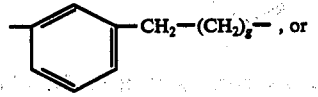

(1)

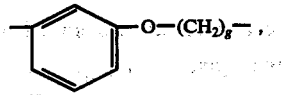

(2)

wherein $g$ is one, 2, or 3.

2. A compound according to claim 1, wherein $M_1$ is

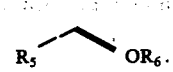

3. A compound according to claim 1, wherein $M_1$ is

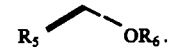

4. A compound according to claim 3, wherein Y is cis—CH=CH—.

5. A compound according to claim 4, wherein $m$ is 3.

6. A compound according to claim 5, wherein $g$ is 3.

7. 2a,2b-Dihomo-3,7-inter-m-phenylene-4,5,6-trinor-15-epi-cis-13-PGD₁, a compound according to claim 6.

8. A compound according to claim 5, wherein $g$ is one.

9. 3,7-Inter-m-phenylene-4,5,6-trinor-15-epi-cis-13-PGD₁, a compound according to claim 8.

10. 3,7-Inter-m-phenylene-4,5,6-trinor-3-oxa-15-epi-cis-13-PGD₁, a compound according to claim 8.

11. A compound according to claim 3, wherein Y is trans—CH=CH—.

12. A compound according to claim 11, wherein $m$ is 3.

13. A compound according to claim 12, wherein $Z_9$ is

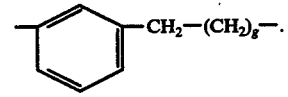

14. A compound according to claim 13, wherein $g$ is 3.

15. A compound according to claim 13, wherein $g$ is one.

16. A compound according to claim 15, wherein $R_5$ and $R_6$ are both hydrogen.

17. A compound according to claim 16, wherein $R_3$ and $R_4$ are both hydrogen.

18. 3,7-Inter-m-phenylene-4,5,6-trinor-PGD₁, a compound according to claim 17.

19. A compound according to claim 16, wherein $R_3$ and $R_4$ are both fluoro.

20. 16,16-Difluoro-3,7-inter-m-phenylene-4,5,6-trinor-PGD₁, a compound according to claim 19.

21. A compound according to claim 13, wherein $Z_9$ is

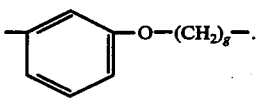

22. A compound according to claim 21, wherein $g$ is 3.

23. A compound according to claim 22, wherein $R_5$ and $R_6$ are both hydrogen.

24. A compound according to claim 23, wherein $R_3$ and $R_4$ are both hydrogen.

25. 2a,2b-Dihomo-3,7-inter-m-phenylene-4,5,6-trinor-3-oxa-PGD$_1$, a compound according to claim 24.

26. A compound according to claim 23, wherein $R_3$ and $R_4$ are both fluoro.

27. 2a,2b-Dihomo-16,16-difluoro-3,7-inter-m-phenylene-4,5,6-trinor-3-oxa-PGD$_1$, a compound according to claim 26.

28. A compound according to claim 21, wherein $g$ is one.

29. A compound according to claim 28, wherein $R_5$ and $R_6$ are both hydrogen.

30. A compound according to claim 29, wherein $R_3$ and $R_4$ are both hydrogen.

31. 3,7-Inter-m-phenylene-4,5,6-trinor-3-oxa-PGD$_1$, a compound according to claim 30.

32. A compound according to claim 29, wherein $R_3$ and $R_4$ are both fluoro.

33. 16,16-Difluoro-3,7-inter-m-phenylene-4,5,6-trinor-3-oxa-PGD$_1$, a compound according to claim 32.

* * * * *

UNITED STATES PATENT OFFICE
CERTIFICATE OF CORRECTION

Patent No. 4,066,836  Dated January 3, 1978

Inventor(s) Douglas Ross Morton, Jr.

It is certified that error appears in the above-identified patent and that said Letters Patent are hereby corrected as shown below:

[21] Appl. No.: should read -- 755,980 --.

Signed and Sealed this

Thirtieth Day of May 1978

[SEAL]

Attest:

RUTH C. MASON  
Attesting Officer

LUTRELLE F. PARKER  
Acting Commissioner of Patents and Trademarks